(12) United States Patent
Homnick et al.

(10) Patent No.: US 11,992,539 B2
(45) Date of Patent: May 28, 2024

(54) CURABLE DENTAL COMPOSITIONS AND USES THEREOF

(71) Applicant: Solventum Intellectual Properties Company, Maplewood, MN (US)

(72) Inventors: Paul J. Homnick, Lake Elmo, MN (US); Ahmed S. Abuelyaman, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/032,655

(22) PCT Filed: Nov. 3, 2021

(86) PCT No.: PCT/IB2021/060177
§ 371 (c)(1),
(2) Date: Apr. 19, 2023

(87) PCT Pub. No.: WO2022/112886
PCT Pub. Date: Jun. 2, 2022

(65) Prior Publication Data
US 2023/0404861 A1      Dec. 21, 2023

Related U.S. Application Data

(60) Provisional application No. 63/118,361, filed on Nov. 25, 2020.

(51) Int. Cl.
| A61K 6/887 | (2020.01) |
| A61K 6/16 | (2020.01) |
| A61K 6/17 | (2020.01) |
| A61K 6/71 | (2020.01) |

(52) U.S. Cl.
CPC ............... *A61K 6/887* (2020.01); *A61K 6/16* (2020.01); *A61K 6/17* (2020.01); *A61K 6/71* (2020.01)

(58) Field of Classification Search
CPC .................................................. A61K 6/887
See application file for complete search history.

(56) References Cited

U.S. PATENT DOCUMENTS

| | | | |
|---|---|---|---|
| 3,347,954 A | 10/1967 | Hellmut et al. | |
| 3,541,068 A | 11/1970 | Taylor | |
| 3,729,313 A | 4/1973 | Smith | |
| 3,741,769 A | 6/1973 | Smith | |
| 3,808,006 A | 4/1974 | Smith | |
| 4,071,424 A | 1/1978 | Dart et al. | |
| 4,250,053 A | 2/1981 | Smith | |
| 4,394,403 A | 7/1983 | Smith | |
| 4,443,587 A | 4/1984 | Schmitt et al. | |
| 4,544,742 A | 10/1985 | Schmitt et al. | |
| 4,642,126 A | 2/1987 | Zador et al. | |
| 4,652,274 A | 3/1987 | Boettcher et al. | |
| 4,737,593 A | 4/1988 | Ellrich et al. | |
| 5,332,429 A | 7/1994 | Mitra et al. | |
| 5,545,676 A | 8/1996 | Palazzotto et al. | |
| 6,572,693 B1 | 6/2003 | Wu et al. | |
| 6,730,156 B1 | 5/2004 | Windisch et al. | |
| 6,899,948 B2 | 5/2005 | Zhang et al. | |
| 7,579,066 B2 | 8/2009 | Nozawa et al. | |
| 8,399,569 B2 | 3/2013 | Murofushi et al. | |
| 8,647,510 B2 | 2/2014 | Kolb et al. | |
| 8,722,759 B2 | 5/2014 | Craig | |

(Continued)

FOREIGN PATENT DOCUMENTS

| DE | 1495520 A1 | 4/1969 |
| EP | 0059451 B1 | 7/1985 |

(Continued)

OTHER PUBLICATIONS

He, "Preparation and characterization of Bis-GMA-free dental composites with dimethacrylate monomer derived from 9,9-Bis[4-(2-hydroxyethoxy)phenyl]fluorene" Dental Materials, Jul. 2018, vol. 34, No. 7, pp. 1003-1013.

International Search Report for PCT International Application No. PCT/IB2021/060177, dated Jan. 18, 2022, 5 pages.

Moszner, "Benzoyl germanium derivatives as novel visible light photoinitiators for dental materials", Dental Materials, Jul. 2008, vol. 24, No. 7, pp. 901-907.

(Continued)

*Primary Examiner* — Michael F Pepitone
(74) *Attorney, Agent, or Firm* — Kevin Weber

(57) ABSTRACT

A curable dental composition includes a compound having structural formula (A) where X is an amine-, oxygen-, or sulfur-containing linkage; Y is an amine-, oxygen-, or sulfur-containing linkage; n is 1-15; m is 1-5; p is 1-5, with the proviso that when p is greater than 1, m is 1; each $R_1$ is, independently, an alkyl or aryl group having 2 to 20 carbon atoms that is linear, branched, cyclic, or some combination thereof, and optionally includes one or more heteroatoms or unsaturated bonds; and each $R_2$ is, independently, a hydrogen atom or $CH_3$ The composition also includes filler. The filler is present in an amount of at least 25 wt.-%, based on the total weight of the curable dental composition.

11 Claims, No Drawings

(56) References Cited

U.S. PATENT DOCUMENTS

| | | |
|---|---|---|
| 9,056,043 B2 | 6/2015 | Joly et al. |
| 9,295,617 B2 | 3/2016 | Eckert et al. |
| 2001/0051672 A1 | 12/2001 | Albert et al. |
| 2003/0008967 A1 | 1/2003 | Hecht et al. |
| 2013/0109777 A1 | 5/2013 | Eckert et al. |

FOREIGN PATENT DOCUMENTS

| | | | |
|---|---|---|---|
| EP | 2008636 A1 | | 12/2008 |
| EP | 3895682 A1 | | 10/2021 |
| JP | 2012025826 A | * | 2/2012 |
| WO | 2009151957 A1 | | 12/2009 |
| WO | 2012112321 A2 | | 8/2012 |
| WO | 2020122192 A1 | | 6/2020 |

OTHER PUBLICATIONS

Sakaguchi, "Testing of Dental Materials and Biomechanics" Craig's Restorative Dental Materials, 13th Edition., (2012), p. 86.

* cited by examiner

CURABLE DENTAL COMPOSITIONS AND USES THEREOF

CROSS REFERENCE TO RELATED APPLICATIONS

This application is a national stage filing under 35 U.S.C. 371 of PCT/IB2021/060177, filed Nov. 3, 2021, which claims the benefit of U.S. Provisional Application No. 63/118,361, filed Nov. 25, 2020, the disclosures of which are incorporated by reference in their entireties herein.

FIELD

The present disclosure relates to compositions and methods useful in the dental field.

BACKGROUND

Various dental materials are described in, for example, U.S. Pat. App. Pub. 2013/0109777, International Pub. WO2012/112321, U.S. Pat. Nos. 9,056,043, 8,399,569, and 7,579,066.

DETAILED DESCRIPTION

Dental composites are used under highly demanding conditions, These materials are used in the mouth and, therefore, exposed to rapid thermocycling; extreme crushing, grinding, and flexural forces; saliva; and more than 500 species of bacteria.

In addition to withstanding aggressive environmental conditions, the dental composites should also be biocompatible and highly esthetic. Still further, dental composites are especially challenging to develop due to the tight window of desired "handling" properties (e.g. stickiness, stiffness, feathering). Furthermore, these composites must be fast and easy to cure on demand (usually via light curing using 450 nm blue light), and cannot produce excessive shrinkage stress on the tooth/adhesive/filling interfaces during the curing process. Ideally, light-cured dental composites should provide a good degree of cure even in very deep restorations when placed in one large increment (saves time and helps prevent contamination and/or restoration re-do).

Typically, dental composites include one or more filler materials, which impart strength to the composite, dispersed in a matrix or resin. Generally, matching of the refractive indices of the matrix and the filler materials is desirable in that it facilitates achievement of an aesthetically pleasing restoration across a broad class of color shades, as well as contributes to a strong degree of cure even in relatively deep restorations. The filler materials, however, often have a relatively high refractive index, which makes matching of refractive indices of the filler and matrix problematic. Consequently, matrix materials having high refractive indices (such that they match or closely approximate the refractive indices of the filler materials), and that also yield a dental composite exhibiting the numerous above-discussed advantageous properties are desirable.

As discussed above, filler materials impart strength to the dental composites. As filler loading increases, however, the viscosity of the composite tends to increase, which can negatively impact processability/flowability of the composite for the dental practitioner. Consequently, matrix materials that contribute to relatively low viscosities (even at high filler loadings) while also exhibiting the above-discussed relatively high refractive indices, and while still further producing dental composites that exhibit the numerous additional above-discussed advantageous properties are desirable.

As used herein:

The term "cured composition" refers to the reaction product of a curable composition.

The term "visible light" is used to refer to light having a wavelength of about 400 to about 800 nanometers (nm).

A "dental composition" is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min or 1 min. Higher temperatures are not recommended as they might cause pain to the patient and may be detrimental to the patient's health.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

A "curable composition" or "hardenable composition" is a composition or material which can be cured or solidified e.g. by heating to cause polymerization, chemical crosslinking, radiation-induced polymerization or crosslinking or using a redox initiator. A curable composition may contain only one, two, three or more polymerizable groups.

A "curing, hardening, or setting reaction" is used interchangeably and refers to a reaction wherein physical properties such as viscosity and hardness of a curable composition changes over the time due to a chemical reaction between the individual components.

A "cured composition" is the reaction product of a curable composition.

A "nano-sized filler" is a filler, the individual particles thereof have a size in the region of nanometers, e.g. an average particle diameter of less than about 200 nm. Useful examples are given in U.S. Pat. Nos. 6,899,948 and 6,572,693, the content of which especially with regard to nano-sized silica particles is herein incorporated by reference.

An "initiator or initiator system" is a substance being able to start the curing process of a hardenable compound.

"Ambient conditions" mean the conditions which the compositions of the present disclosure are usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.). As used herein, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about."

In some embodiments, the present disclosure is directed to curable dental compositions providing a good balance of desirable properties. Specifically, the curable dental compositions of the present disclosure, which include a desirable matching of refractive indices between resin and filler, exhibit surprisingly low viscosity while also exhibiting strength, handling, cure time, depth of cure, volume shrinkage, shrinkage stress, aesthetic, and biocompatibility properties requisite of a high performing dental composition.

In some embodiments, the curable dental compositions of the present disclosure include a polymerizable resin (or matrix) and a filler dispersed in the resin. The polymerizable resin may include a compound having structural formula (A):

wt.-%, at least 10 wt.-%, at least 20 wt.-%, or at least 40 wt.-%; or between 5 and 25 wt.-%, or between 10 and 40 wt.-%, based on the total weight of the curable dental composition (including filler). If desired, different compounds falling within the definition of compound (A) can be present in the composition (e.g., the curable dental composition may contain two, three, four or even more compounds within structural formula (A), which differ from each other).

In some embodiments, the refractive index of compound (A) may be between 1.53 and 1.60 ($n_D^{20}$), or between 1.53 and 1.58 ($n_D^{20}$).

In some embodiments, the viscosity of compound (A) is no more than 1000 Pa*s, no more than 2000 Pa*s, no more than 3000 Pa*s, no more than 3300 Pa*s, or no more than 3500 Pa*s at 25 degrees Celsius. For purposes of the present disclosure, viscosity may be determined in accordance with the description in the Examples below.

In some embodiments, the curable dental compositions of the present disclosure may include one or more fillers. In some embodiments, the one or more fillers may include inorganic metal oxide materials. In some embodiments, useful fillers may include fumed silica, fillers based on fluoroaluminosilicate glasses, quartz, ground glasses, non-water-soluble fluorides such as $CaF_2$, silica gels such as

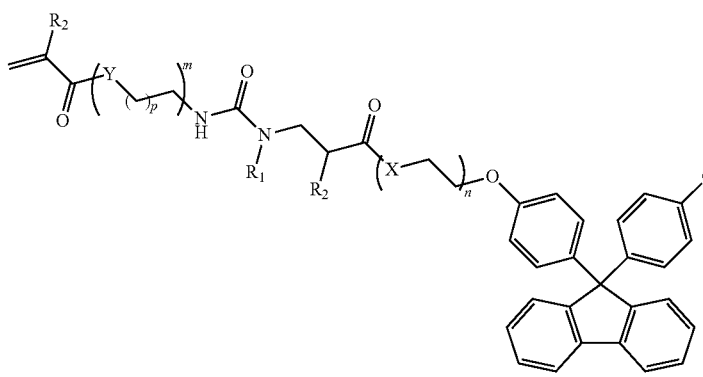
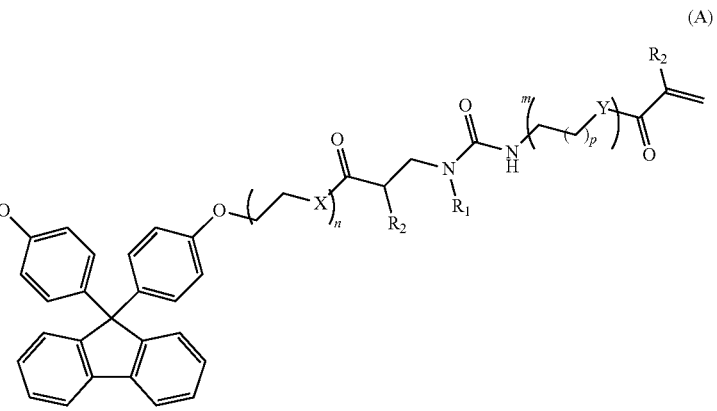

(A)

where
X is an amine-, oxygen-, or sulfur-containing linkage;
Y is an amine-, oxygen-, or sulfur-containing linkage;
n is 1-15, 1-10, or 1-3;
m is 1-5, 1-4, 1-3, or 1-2;
p is 1-5, 1-4, 1-3, or 1-2; with the proviso that when p is greater than 1, m is 1;
each $R_1$ is, independently, an alkyl or aryl group having 2 to 20, 4 to 10, 4 to 7, or 4 to 6 carbon atoms that may be linear, branched, cyclic, or some combination thereof, and may also include one or more heteroatoms or unsaturated bonds; and
each $R_2$ is, independently, a hydrogen atom or $CH_3$.

In some embodiments, each $R_1$ is, independently, selected from the following:

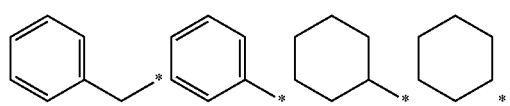

In some embodiments, compound (A) may be present in the curable dental composition in an amount of at least 5 silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate, or combinations thereof.

In some embodiments, the fillers may be either particulate or fibrous in shape. Particulate fillers may generally be understood as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs.

In some embodiments, the size of the fillers should be such that a homogeneous mixture with the polymerizable resin component(s) can be obtained.

In some embodiments, the fillers may have a primary particle size of no greater than 100 nm. As used herein, primary particle size refers to the size of a discrete, unaggregated particle. The fillers can have a unimodal or polymodal (e.g., bimodal) particle size distribution.

In some embodiments, the fillers have an average particle size of at least about 2, 3, 4, or 5 nm; and have an average particle size no greater than about 50, 40, 30, 25, 15, or 10 nm. As used herein, average size (e.g., in terms of diameter) of a particle is based on a TEM (transmission electron microscopy) method, whereby a population is analyzed to obtain an average particle diameter.

In some embodiments, useful silica particles may be substantially spherical and substantially non-porous. Although the silica is may be essentially pure, it may contain small amounts of a stabilizing ion such as ammonium and alkaline metal ions.

Suitable fumed silicas include for example, products sold under the tradename AEROSIL series OX-50, -130, -150, and -200 available from Degussa AG, (Hanau, Germany), and CAB-O-SIL M5 available from Cabot Corp (Tuscola, Ill.).

In some embodiments, useful fluoroaluminosilicate glasses include silanol treated fluoroaluminosilicate glass fillers, as described in U.S. Pat. No. 5,332,429, the disclosure of which is expressly incorporated by reference herein. For example, a fluoride releasing glass may be added to the dental composition to provide the benefit of long-term release of fluoride in use, for example in the oral cavity.

In some embodiments, heavy metal oxide fillers can be included in the curable dental compositions to provide a radiopacity. In this regard, heavy metal oxide may be present in the dental composition in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 can be preferred. The heavy metal oxide should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, the aggregated particles may be less than 200 nm in average diameter or less than 90 nm in average diameter.

In some embodiments, the fillers may include nano-sized silica. Suitable nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Texas (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T40AS); Akzo Nobel Chemicals GmbH, Leverkusen, Germany (for example, those available under the product designation LEVASIL, e.g., 50/50%, 100/45%, 200/30%, 200A/30%, 200/40%, 200A/40%, 300/30% and 500/15%), and Bayer MaterialScience AG, Leverkusen, Germany (for example, those available under the product designation DISPERCOLL S, e.g., 5005, 4510, 4020 and 3030).

In some embodiments, the nano-sized silica particles may be surface treated to, for example, facilitate a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. In some embodiments, the surface-treatment may stabilize the nano-sized particles so that the particles will be well dispersed in the polymerizable resin and result in a substantially homogeneous composition. Furthermore, the silica may be modified over at least a portion of its surface with a surface treatment agent so that the stabilized particle can copolymerize or otherwise react with the polymerizable resin during curing.

In some embodiments, the silica particles can be treated with a resin-compatibilizing surface treatment agent.

In some embodiments, suitable fillers for the curable dental compositions described herein may include nanocluster fillers, such as described in U.S. Pat. No. 6,730,156 (Windisch et al.), U.S. Pat. No. 6,572,693 (Wu et al.), and U.S. Pat. No. 8,722,759 (Craig). In some embodiments, the filler comprises nanoparticles in the form of nanoclusters, i.e. a group of two or more particles associated by relatively weak, but sufficient intermolecular forces that cause the particles to clump together, even when dispersed in a hardenable resin. Suitable nanoclusters can include a loosely aggregated substantially amorphous cluster of non-heavy metal oxide (e.g. silica) particles, and heavy metal oxide (i.e. having an atomic number greater than 28) such as zirconia. The zirconia can be crystalline or amorphous. In some embodiments, the zirconia may be present as a particle. The particles from which the nanocluster is formed preferably have an average diameter of less than about 100 nm. However, the average particle size of the loosely aggregated nanocluster is typically considerably larger.

In some embodiments, the fillers may be present in the curable dental compositions of the present disclosure in an amount of at least 25 wt.-%, at least 30 wt.-%, at least 40 wt.-%, or at least 50 wt.-%; or between 20 and 90 wt.-%, or between 60 and 80 wt.-%, based on the total weight of the curable dental composition.

In some embodiments, the nanocluster fillers may be present in the curable dental compositions in an amount of least 60, 61, 62, 63, 64, or 65 wt-%, based on the total weight of the curable dental composition. The maximum amount of nanocluster filler may be no greater than 75% or 80%. In some embodiments, the total amount of inorganic metal oxide material (i.e. nanoparticle and filler) may be at least 70, 71, 72, 73, 74, or 75 wt.-%, based on the total weight of the curable dental composition. The maximum amount of inorganic metal oxide material (i.e. nanoparticle and filler) is typically no greater than 80% or 85%.

In some embodiments, the refractive index of any or all of the filler materials may be between 1.4 and 2.7. In some embodiments, a plurality of fillers having different refractive indices may be employed. In such embodiments, the fillers may include at least 30 wt. %, at least 40 wt. %, or at least 50 wt. % of filler having a refractive index greater than 1.5, based on the total weight of the fillers.

In some embodiments, mixtures of fillers can be used. When a mixture of fillers is used, an amount of the filler may have a different refractive index than the cured polymerizable resin, inclusive of nanoparticles. In some embodiments, the (e.g. nanocluster) filler particle has a higher refractive index than the organic phase of the polymerizable resin. For example, the (e.g. nanocluster) filler particle may have a refractive index of at least 1.530, 1.535, or 1.540; whereas the organic phase (i.e. in the absence of nanoparticles) of the polymerizable resin may have a lower refractive index.

In some embodiments, the curable dental compositions of the present disclosure may include an initiator or initiator system that starts the curing process of the polymerizable components of the composition. Generally, the curable dental compositions of the present disclosure may be chemically curable, heat curable, or light curable compositions.

Light curable materials should have an appropriate initiator system. Chemically curable materials can be auto-cured (e.g. via redox initiators). Alternatively, the materials can be hardened by a combination of auto- and light-cure. For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between about 200 and about 800 nm.

A variety of visible or near-IR photoinitiator systems may be used for photopolymerization of free-radically polymerizable materials useful in the present disclosure. For example, in free radical polymerization (hardening), a photoinitiation system can be selected from systems which initiate polymerization via a two component system of an amine and an α-diketone as described in U.S. Pat. No. 4,071,424 and WO 2009151957, which are herein incorporated by reference. Alternatively, the resin can be combined with a three component or ternary photoinitiator system such as described in U.S. Pat. No. 5,545,676 and WO 2009151957, which are incorporated herein by reference.

In the ternary photoinitiator system, the first component is an iodonium salt, i.e., a diaryliodonium salt. The iodonium salt is preferably soluble in the monomer and shelf-stable (i e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as Cl$^-$, Br$^-$, I$^-$ or C$_4$H$_5$ SO$_3$$^-$) or a metal complex salt (e.g., containing SbF$_5$OH$^-$ or AsF$_6$$^-$). Mixtures of iodonium salts can be used if desired. Suitable iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, or greater than 400 to 700 nanometers, or greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. In some embodiments, the sensitizers may include ketones (e.g., monoketones or alpha-diketones), ketocoumarins, aminoarylketones or p-substituted aminostyryl ketone compounds. For applications requiring high sensitivity, a sensitizer containing a julolidinyl moiety may be employed. For applications requiring deep cure (e.g., cure of highly-filled composites), sensitizers having an extinction coefficient below about 1000 or below about 100, at the desired wavelength of irradiation for photopolymerization, may be employed. Alternatively, dyes that exhibit reduction in light absorption at the excitation wavelength upon irradiation can be used.

The third component of a ternary initiator system may be a donor. Suitable donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. In some embodiments, donors contain an electron donor atom such as a nitrogen, oxygen, phosphorus, or sulfur atom, and an abstractable hydrogen atom bonded to a carbon or silicon atom alpha to the electron donor atom. A wide variety of donors are disclosed in U.S. Pat. No. 5,545,676, which is incorporated herein by reference.

Alternatively, type-I free-radical initiators useful in the present disclosure may include the class of acylphosphine oxides, as described in U.S. Pat. No. 4,737,593. Such acylphosphine oxides are of the general formula

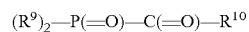

$(R^9)_2$—P(=O)—C(=O)—R$^{10}$ wherein each R$^9$ individually can be a hydrocarbyl group such as alkyl, cycloalkyl, aryl, and aralkyl, any of which can be substituted with a halo-, alkyl- or alkoxy-group, or the two R$^9$ groups can be joined to form a ring along with the phosphorous atom, and wherein R$^{10}$ is a hydrocarbyl group, an S-, O-, or N-containing five- or six-membered heterocyclic group, or a —Z—C(=O)—P(=O)—(R$^9$)$_2$ group, wherein Z represents a divalent hydrocarbyl group such as alkylene or phenylene having from 2 to 6 carbon atoms.

Suitable acylphosphine oxides useful in the present disclosure may include those in which the R$^9$ and R$^{11}$ groups are phenyl or lower alkyl- or lower alkoxy-substituted phenyl. By "lower alkyl" and "lower alkoxy" is meant such groups having from 1 to 4 carbon atoms. In some embodiments, the acylphosphine oxide is bis(2,4,6-trimethylbenzoyl)phenyl phosphine oxide (IRGACURE™ 819, Ciba Specialty Chemicals, Tarrytown, NY).

Tertiary amine reducing agents may be used in combination with an acylphosphine oxide. Illustrative tertiary amines include ethyl 4-(N,N-dimethylamino)benzoate and N,N-dimethylaminoethyl methacrylate. Similarly, benzoyl germanium can be used as a type-I initiator (Moszner et al, Dental Materials, [2008], vol 24, pages 901-907).

Another free-radical initiator system that can alternatively be used in the dental materials of the present disclosure includes the class of ionic dye counterion complex initiators comprising a borate anion and a complementary cationic dye.

In some embodiments, heat may be used to initiate the hardening, or polymerization, of free radically active groups. Examples of heat sources suitable for the dental materials of the present disclosure include inductive, convective, and radiant. Thermal sources should be capable of generating temperatures of at least 40° C. under normal conditions or at elevated pressure. This procedure is preferred for initiating polymerization of materials occurring outside of the oral environment.

Organic peroxide compounds together with so-called activators are also suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable activators include, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451). Preferred malonyl sulfamides are 2,6-dimethyl-4-isobutyl-malonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

In some embodiments, the initiator(s) may be present in the curable dental composition in an amount of at least 0.03 wt.-%, at least 0.1 wt.-%, at least 0.2 wt.-%, or at least 0.3 wt.-%, based on the total weight of the curable dental composition (including fillers); and up to 3 wt.-%, up to 2 wt.-%, or up to 1.8 wt-%, based on the total weight of the curable dental composition (including fillers).

According to some embodiments, the curable dental compositions may include a further polymerizable component that is different from compound (A). Such further polymerizable component may include a free-radically polymerizable material, including ethylenically unsaturated monomer, monomers or oligomers or polymers. Such further polymerizable components may include at least one ethylenically unsaturated bond, and be capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate; polyfunctional (meth)acrylates comprising urethane, urea or amide groups, as those of EP 2007111356, herewith incorporated by reference. Mixtures of two or more of these free radically polymerizable materials can be used, if desired.

In some embodiments, the further polymerizable component(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

In some embodiments, the further polymerizable component(s) may be present in the composition in an amount of at least about 5 wt.-% or at least about 10 wt.-%, based on the total weight of the curable dental composition; or from 5 to 65 wt.-%, from 10 to 55 wt.-%, or from 10 to 40 wt.-%, based on the total weight of the curable dental composition.

In some embodiments, the curable dental composition may also include one or more softeners. Suitable softeners may include hydroxyl functionalities. If present, softeners may contain two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights. The hydroxyl group containing material can optionally contain other functionalities that do not substantially interfere with cationic polymerization at room temperature. Thus, the hydroxyl group containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl group containing material can, for example, be selected from naturally occurring or synthetically prepared cellulosic materials. Of course, the hydroxyl group containing material is also substantially free of groups that may be thermally or photolytically unstable;

that is, the material will not decompose or liberate volatile components at temperatures below about 100° C. or in the presence of actinic light that may be encountered during the desired polymerization conditions for the photo-copolymerizable composition. In some embodiments, softeners may be present in the composition in an amount up to about 10 wt.-% or up to about 15 wt.-% or up to about 20 wt.-%.

In some embodiments, the curable dental compositions may also contain suitable adjuvants such as accelerators, inhibitors or retarders, absorbers, stabilizers, pigments, dyes, surface tension depressants and wetting aids, antioxidants, and other ingredients well known to those skilled in the art. The amounts and types of each ingredient in the composition may be adjusted to provide the desired physical and handling properties before and after polymerization. For example, the polymerization rate, polymerization stability, fluidity, compressive strength, tensile strength and durability of the dental material may be adjusted in part by altering the types and amounts of polymerization initiator(s) and, if present, the loading and particle size distribution of filler(s).

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive functionality so that they will be copolymerized with the resin.

As discussed above, the curable dental compositions of the present disclosure (as well as the cured dental compositions that result from the curable compositions) provide a good balance of desirable properties. Specifically, the curable (or cured) dental compositions may include a desirable matching of refractive indices between resin and filler, exhibit surprisingly low viscosity while also exhibiting strength, handling, cure time, depth of cure, volume shrinkage, shrinkage stress, aesthetic, and biocompatibility properties requisite of a high performing dental composition. In this regard, the curable dental compositions may exhibit
  a refractive index of the cured polymerizable resin inclusive of nanoparticles (i.e., the cured dental composition exclusive of particles greater than 100 nm in size) differs from the refractive index of the (e.g. inorganic metal oxide) filler by less than 0.05, less than 0.03, less than 0.02, less than 0.01, or less than 0.005
  a viscosity sufficiently low to provide flowabity and sculptability characteristics requiste of commercial dental composites (and thus good injectability and flowabilty characteristics pre-cure for easily and quickly constructing the desired dental anatomy).
The curable dental compositions may further exhibit:
  a good filler/pigment wettability (e.g. useful to achieve comparably high filler loads),
  a comparably high molecular weight (e.g. useful to achieve comparably low polymerization shrinkage during or after curing, if desired),
  a comparably high hydrophobicity (e.g. useful to achieve comparably low water uptake and/or exogenic staining),
  low shrinkage stress during or after curing (e.g. useful for avoiding post-op sensitivity and ensuring long-term marginal integrity),
  a high depth of cure (e.g. useful for bulk cure applications, if desired),
  comparably high flexural strength
  a medium E-Modulus at standard wear resistance (measured according to ACTA).
    Compositions with appropriate E-Modulus typically contribute to the provision of compositions with comparably low brittleness.

In some embodiments, the curable dental compositions may be hardened in an acceptable time frame, e.g., less than 120 seconds (s), less than 100 s, less than 60 s, or less than 30 s, and to a sufficient depth using visible light source equipment already available in the dental office or electronics fabrication facilities.

In some embodiments, the present disclosure is further directed to a method of making a curable dental composition. The curable dental compositions can be obtained by combining (including mixing or kneading) the individual components of the composition, preferably under "safe light" conditions. Suitable inert solvents may be employed if desired when providing the mixture. Any solvent may be used which does not react appreciably with the components of the curable dental compositions. Examples of suitable solvents include acetone, dichloromethane, acetonitrile and lactones.

In some embodiments, the present disclosure further relates to the use of the curable compositions described herein for producing a dental cement, a crown and bridge material, a dental filling material, a casting material, a cavity liner, a coating composition, a mill blank, an orthodontic devices, a sealant, or combinations thereof.

In some embodiments, the present disclosure further relates to the use of the curable dental composition in a dental procedure, the process of using comprising the steps of
  a) placing the curable dental composition in contact with a surface of a tooth; and
  b) hardening the curable dental composition.

In some embodiments, the curable dental compositions are particularly well adapted for use as a wide variety of dental materials, which may be filled or unfilled. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

When the dental composition is applied to a tooth, the tooth can optionally be pre-treated with a primer such as dentin or enamel adhesive by methods known to those skilled in the art. The dental compositions can be used for example, as artificial crowns, anterior or posterior fillings, casting materials, cavity liners, cements, coating compositions, mill blanks, orthodontic devices, restoratives, prostheses and sealants.

In some embodiments, the curable dental compositions may be used as a dental filling material. The dental filling materials can be placed directly in the mouth and cured (hardened) in situ, or alternatively, may be fabricated into a prosthesis outside the mouth and subsequently adhered in place inside the mouth.

EXAMPLES

Objects and advantages of this disclosure are further illustrated by the following examples, but the particular materials and amounts thereof recited in these examples, as well as other conditions and details, should not be construed to unduly limit this disclosure. These examples are merely for illustrative purposes only and are not meant to be limiting on the scope of the appended claims.

Refractive Index

The refractive index and density of various components commonly utilized in hardenable dental compositions is reported in the literature or provided by the supplier of such material. For components that are not reported in the literature, density and refractive index values can be measured using known and established techniques. For example, mercury porosimetry can be used for determination of density and the refractive index can be measured according to the methods described in the forthcoming examples. The refractive index and density of some representative components are as follows: Table A: Refractive indexes of resins as measured at 25° C.

TABLE A

Refractive indexes of resins as measured at 25° C.

| Resin Name | Refractive Index |
| --- | --- |
| Miramer HR6060 | 1.58 |
| BHEPF-IEEMA (Preparatory Example A) | 1.57 |
| Miramer HR6100 | 1.56 |
| 70:30 Miramer HR6060:UDMA | 1.55 |
| BisGMA | 1.55 |
| 70:30 BHEPF-IEEMA:UDMA | 1.55 |
| 70:30 HR6100:UDMA | 1.54 |
| Bisphenol-S DMA | 1.54 |
| Miramer HR6200 | 1.53 |
| BisEMA6 | 1.52 |
| 70:30 HR6200:UDMA | 1.52 |
| T-Diol IEM | 1.50 |
| T-Diolat | 1.49 |
| X 852 | 1.49 |
| UDMA | 1.49 |
| TEGDMA | 1.46 |

Refractive Index Determination: For uncured samples, refractive indices were measured with a Bausch & Lomb refractometer at 25° C., using the sodium "D" line (~589 am).

TABLE 1

Materials used for monomer synthesis and composite compounding

| Structure | Name | Abbreviation | CAS # | Supplier |
| --- | --- | --- | --- | --- |
| 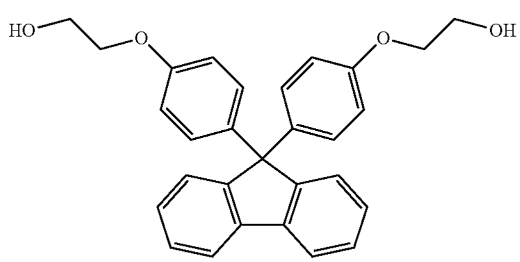 [SMILES: OCCOc1ccc(C2(c3ccc(OCCO)cc3)c3ccccc3-c3ccccc32)cc1] | 9,9-Bis[4-(2-hydroxyethoxy)phenyl]fluorene | BHEPF | 117344-32-8 | TCI America |
| 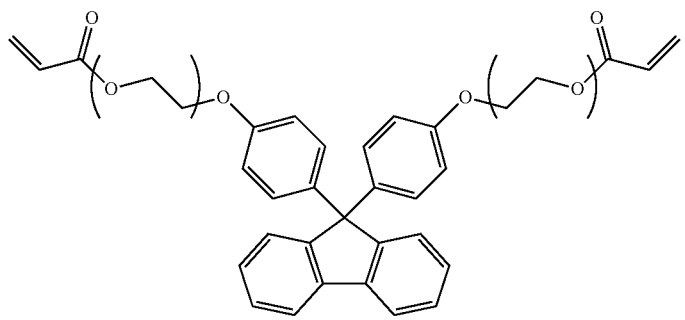 | Modified Bisphenol fluorene diacrylate | Miramer HR6060 | — | Miwon Specialty Chemical Co. Ltd |

TABLE 1-continued

Materials used for monomer synthesis and composite compounding

| Structure | Name | Abbreviation | CAS # | Supplier |
|---|---|---|---|---|
| [structure] | Modified Bisphenol fluorene diacrylate | Miramer HR6200 | — | Miwon Specialty Chemical Co. Ltd |
| [structure] | Karenz MOI™-EG | IEEMA | 107023-60-9 | Showa Denko Europe GmbH |
| [structure] | Karenz MOI™ | IEMA | | Showa Denko Europe GmbH |
| [structure] | Dibutyltin Dilaurate | DBTDL | 77-58-7 | Sigma-Aldrich |
| [structure] | Ethyl Acetate | EtOAc | 141-78-6 | Sigma-Aldrich |
| $MgSO_4$ | Anhydrous Magnesium Sulfate | $MgSO_4$ | 7487-88-9 | Sigma-Aldrich |
| [structure] | Urethane Dimethacrylate (mixture of isomers) | UDMA | 72869-86-4 | Sigma-Aldrich |

Other Components:

"YbF3" refers to ytterbium fluoride, approximately 100-105 nm particle size, refractive index 1.52 available from Sukgyung AT Co. Ltd., (Korea).

"S/T Silica/Zirconia Clusters" refers to silane-treated silica-zirconia nanocluster filler, prepared generally as described in U.S. Pat. No. 6,730,156 at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of ~8.8 with aqueous $NH_4OH$ (rather than to a pH of 3-3.3 with trifluoroacetic acid), and obtaining the nanocluster filler by gap drying (rather than spray drying).

"S/T 20 nm Silica" refers to silane-treated silica nanoparticle filler having a nominal particle size of approximately 20 nanometers, prepared substantially as described in U.S. Pat. No. 6,572,693 at column 21, lines 63-67 ("Nanosized particle filler, Type #2").

"S/T Nanozirconia" refers to silane-treated zirconia filler, which was prepared from the zirconia sol substantially as described in U.S. Pat. No. 8,647,510 at column 36 line 61 to column 37, line 16 (Example 11A-IER). The zirconia sol was added to an equivalent weight of 1-methoxy-2-propanol containing GF-31 (1.1 mmol of GF-31 per gram of nanozirconia to be surface treated). The mixture was heated to ~85° C. for 3 hours with stirring. The mixture was cooled to 35° C., adjusted to a pH of ~9.5 with aqueous $NH_4OH$, and the mixture reheated to ~85° C. for 4 hours with stirring. The resultant material was washed with an excess of water, and t S/T Nanozirconia was isolated as a dry powder via gap drying to remove solvents. As used herein, "S/T Nanozirconia" also refers to silane-treated zirconia filler which is solvent exchanged into the resins (and pastes) without isolating the S/T Nanozirconia in dry powder form (e.g., by addition of the S/T Nanozirconia sol to a methacrylate-containing resin, followed by concentration at reduced pressure and/or heating to remove volatiles associated with the sol, as further detailed in the examples herein).

Preparatory Example A

Synthesis of BHEPF-IEEMA Urethane

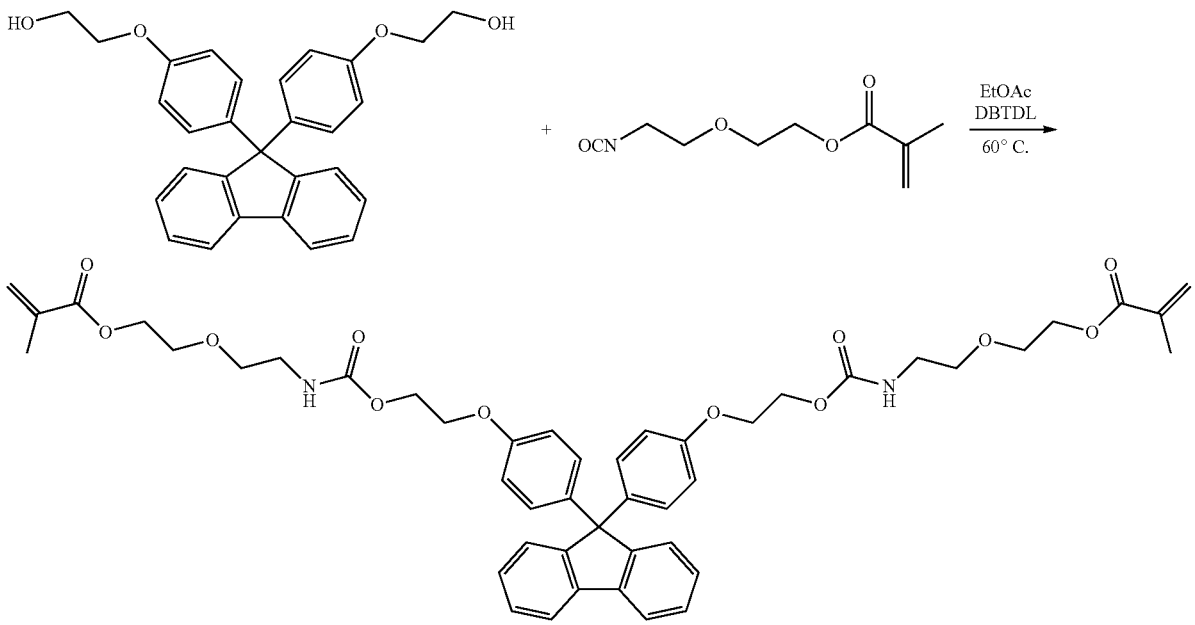

Scheme 1 Synthesis of BHEPF-IEEMA

BHEPF was dried prior to use by dissolving in dichloromethane (DCM), drying over $MgSO_4$, and concentration under vacuum. BHEPF (26.67 g) was suspended in 100 mL dry EtOAc with 24.28 g IEEMA and 4 drops DBTDL. The reaction mixture was heated to 60° C., during which time the reaction mixture became a homogeneous solution. The homogenous reaction mixture was allowed to cool gradually to room temperature, and stirred overnight. The solvent was stripped under vacuum to give BHEPF-IEEMA in quantitative yield as a clear, colorless, viscous liquid. Analysis by H-NMR confirmed the structure, ATR-FTIR confirmed the conversion of isocyanate to urethane.

Preparatory Example B

Synthesis of Miramer HR6200 Butylamine

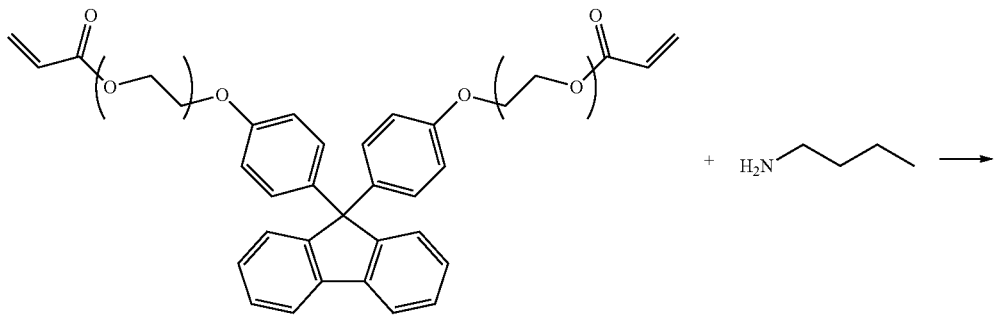

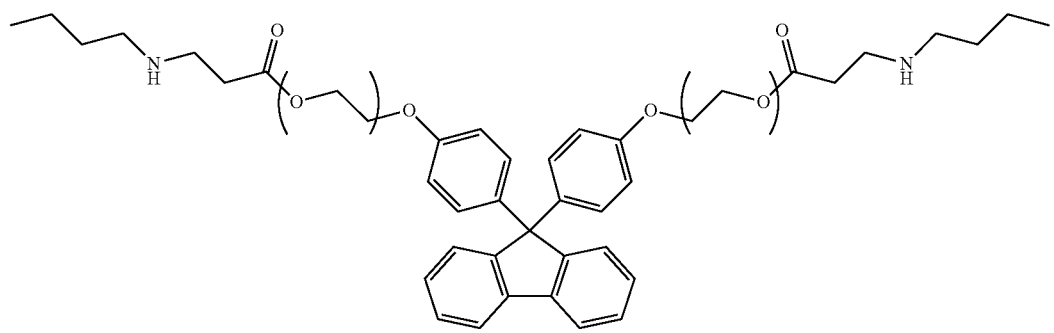
Miramer HR6200 (80.00 g) was combined with n-butylamine (8.68 g). Very mild exotherm was observed (up to 27° C.) prior to heating the reaction mixture to 50° C. for 8 hours. Obtained conjugate addition product in quantitative yield. Analysis by H-NMR confirmed the structure.
Preparatory Example C
Synthesis of Miramer HR6200 Butylamine IEMA Urea
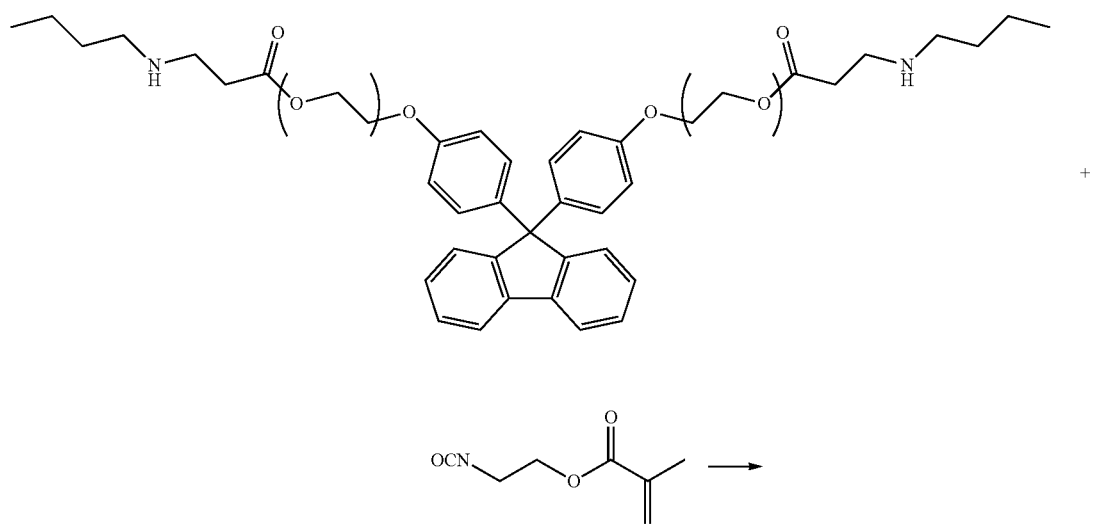
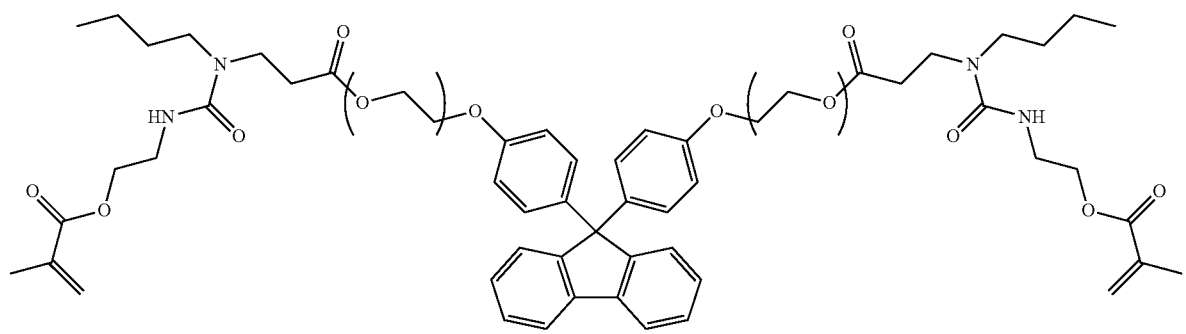

Miramer HR6200 Butylamine (Preparatory Example B) (40.05 g) was charged into a glass jar. IEMA (8.33 g) was added portionwise with stirring. Rate of isocyanate addition was slow enough to keep exotherm under 60° C. Obtained urea product in quantitative yield. Analysis by H-NMR confirmed the structure.

Preparatory Example D

Synthesis of Miramer HR6200 Butylamine IEEMA Urea

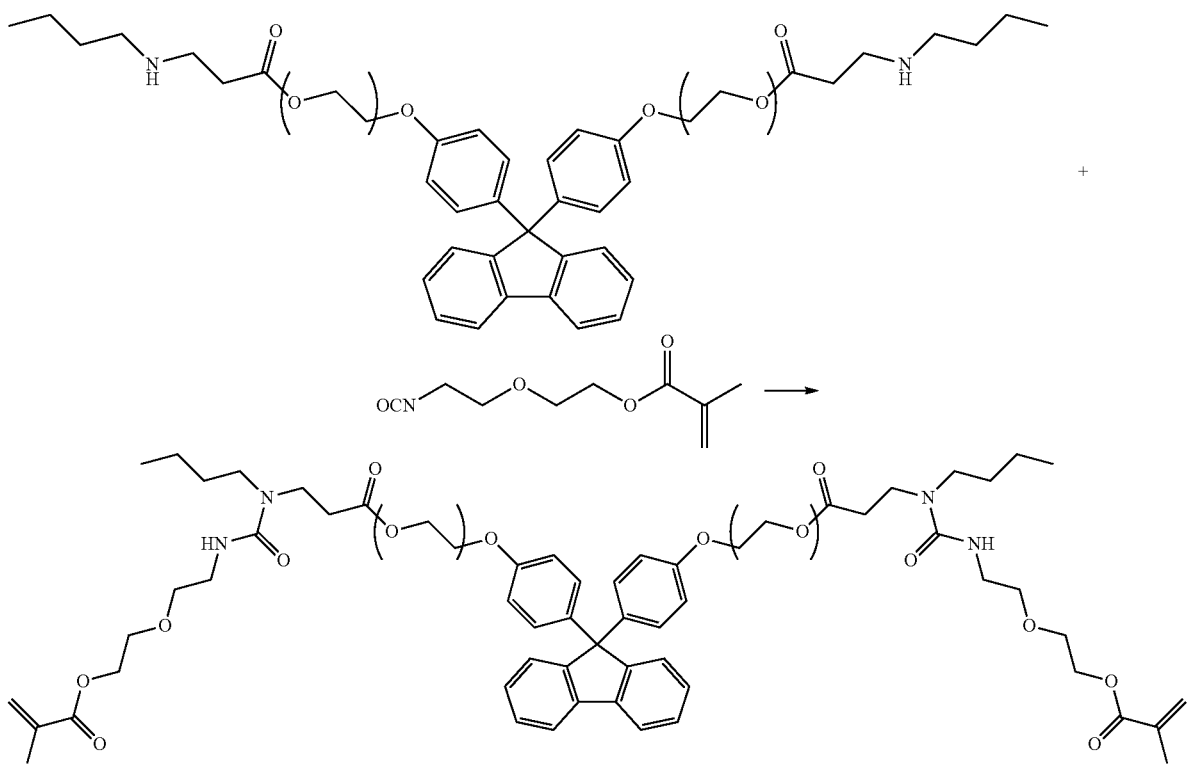

Miramer HR6200 Butylamine (Preparatory Example B) (40.07 g) was charged into a glass jar. IEEMA (10.68 g) was added portionwise with stirring. Rate of isocyanate addition was slow enough to keep exotherm under 60° C. Obtained urea product in quantitative yield Analysis by H-NMR confirmed the structure.

Preparatory Example E

Synthesis of Miramer HR6060 Butylamine

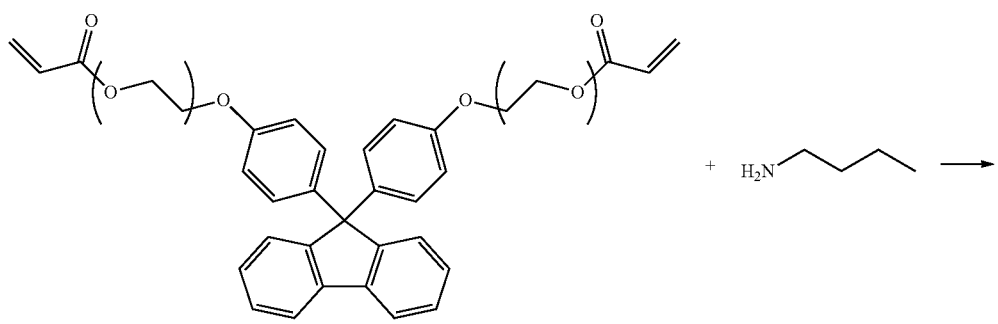

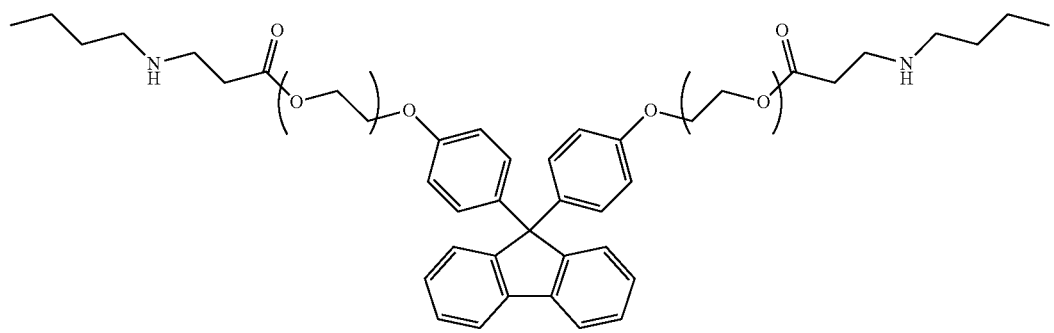
Miramer HR6060 (100.06 g) was combined with n-butylamine (20.04 g). Very mild exotherm was observed (up to 32° C.) prior to heating the reaction mixture to 50° C. for 8 hours. Obtained conjugate addition product in quantitative yield. Analysis by H-NMR confirmed the structure.
Preparatory Example F
Synthesis of Miramer HR6060 Butylamine IEMA Urea
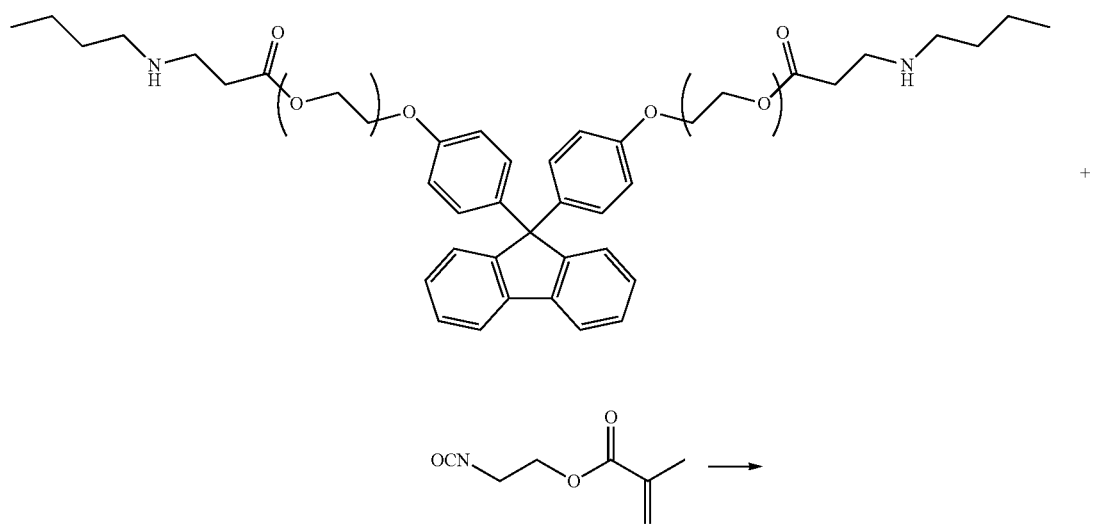
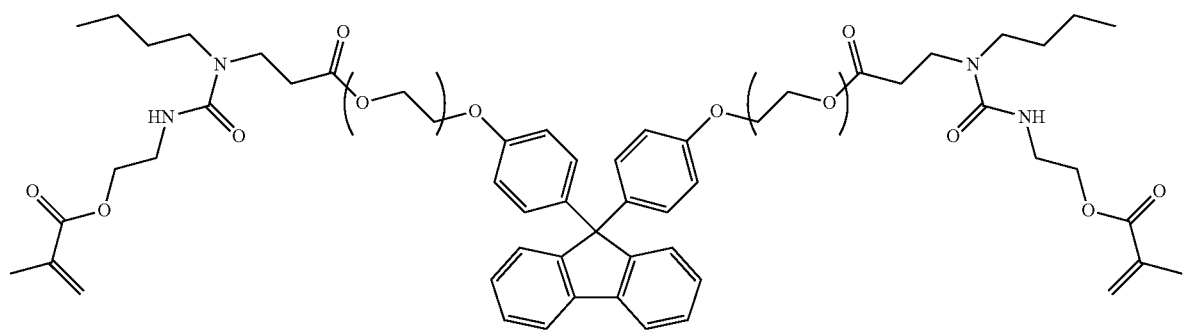

Miramer HR6060 Butylamine (Preparatory Example E) (40.06 g) was charged into a glass jar. IEMA (14.19 g) was added portionwise with stirring. Rate of isocyanate addition was slow enough to keep exotherm under 60° C. Obtained urea product in quantitative yield. Analysis by H-NMR confirmed structure.

Preparatory Example G

Synthesis of Miramer HR6060 Butylamine IEEMA Urea

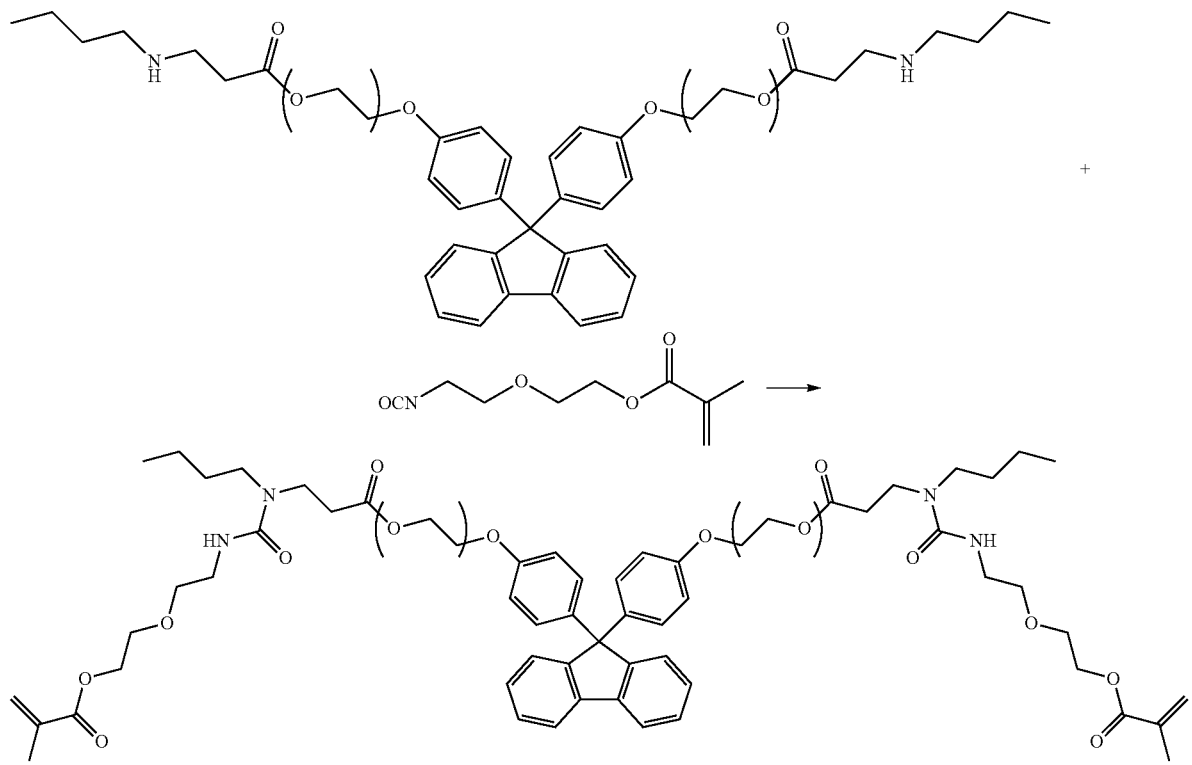

Miramer HR6060 Butylamine (Preparatory Example E) (40.02 g) was charged into a glass jar. IEEMA (18.22 g) was added portionwise with stirring. Rate of isocyanate addition was slow enough to keep exotherm under 60° C. Obtained urea product in quantitative yield. Analysis by H-NMR confirmed structure.

Preparatory Example H—Stock Resin

A stock resin was prepared by combining 14 grams of Preparatory Example A (BHEPF-IEEMA Urethane) with 6 grams of activated UDMA.

Comparative Example C1

Comparative Example C1 was FILTEK Bulk Fill Posterior Restorative product, commercially available from 3M Company, St. Paul, MN, USA.

Example 1 Containing 75% Filler

Example 1 was prepared by combining the following: 5.00 grams of Stock Resin (Preparatory Example H), 12.98 grams of S/T Silica/Zirconia Clusters, 0.32 grams of S/T Nanozirconia, 0.59 grams of S/T 20 nm Silica, and 1.14 grams of YbF3 (ytterbium fluoride).

Example 2 Containing 73% Filler

Example 2 was prepared by combining the following: 5.40 grams of Stock Resin (Preparatory Example H), 12.63 grams of S/T Silica/Zirconia Clusters, 0.31 grams of S/T Nanozirconia, 0.57 grams of S/T 20 nm Silica, and 1.09 grams of YbF3 (ytterbium fluoride).

Example 3 Containing 71% Filler

Example 3 was prepared by combining the following: 5.80 grams of Stock Resin (Preparatory Example H), 12.28 grams of LE filler, 0.30 grams of S/T Nanozirconia, 0.55 grams of S/T 20 nm Silica, and 1.07 grams of YbF3 (ytterbium fluoride).

Physical Properties Testing

Stress Test Method (Cusp Deflection Test)

To measure stress development during the curing process, a slot was machined into a rectangular 15×8×8 mm aluminum block. The slot was 8 mm long, 4 mm deep, and 2 mm across, and was located 2 mm from an edge, thus forming a 2 mm wide aluminum cusp adjacent to a 2 mm wide cavity containing dental compositions being tested. A linear variable displacement transducer (Model GT 1000, used with an E309 analog amplifier, both from RDP Electronics, United Kingdom) was positioned to measure the displacement of the cusp tip as the dental composition photocured at room temperature. Prior to testing, the slot in the aluminum block was sandblasted using Rocatec Plus Special Surface Coating Blasting Material (3M Oral Care), treated with RelyX Ceramic Primer (3M Oral Care, St. Paul, Minn., USA), and finally treated with a commercially available dental adhesive (SCOTCHBOND Universal Adhesive, available from 3M Oral Care). A substantially similar machined aluminum block and testing apparatus are depicted FIGS. 1 and 2 of U.S. Pat. No. 9,056,043 (Joly et al.).

The slot was fully packed with each of the Example Pastes. The material was irradiated for 1 minute with a dental curing light (ELIPAR S-10, 3M Oral Care) positioned almost in contact (<1 mm) with the test material in the slot, then the displacement of the cusp in microns was recorded 9 minutes after the light was extinguished. Numbers closer to 0 indicate lower deflection, and thus lower stresses.

Diametral Tensile Strength

Diametral tensile strength (DTS) was measured per the following procedure. The uncured composite sample was injected into a glass that was about 30 mm long with a 4-mm inside diameter. It was filled about ½ full and capped with silicone rubber plugs. The tube was compressed axially at approximately 3 kg/cm$^2$ pressure for 5 minutes. While still under pressure, the sample was then light cured for 60 seconds by exposure to a dental curing light with a radiant exitance of greater than 1000 mW/cm. The tube was rotated as it cured to ensure equal exposure. A Buehler IsoMet 4000 (Illinois Tool Works, Lake Bluff, Ill., USA) saw was then used to section disks about 2 mm thick from the tube. The resulting disks were stored in distilled water at 37° C. for about 24 hours prior to testing Measurements were carried out using an appropriate materials test frame (e.g., Instron 5966, Instron Corp., Canton, Mass.) with a 10 kilonewton load cell at a crosshead speed of 1 mm per minute. Diametral tensile strength was calculate as describe in Craig's Restorative Dental Materials, (Ronals L. Sakaguchi and John M. Powers. "Testing of Dental Materials and Biomechanics." *Craig's Restorative Dental Materials*, thirteenth ed., Elsevier, 2012, p. 86). Results were reported in MPa. Higher numbers (MPa) indicate greater strengths.

Barcol Hardness Test Method

Barcol Hardness of a test sample was determined according to the following procedure. An uncured composite sample was cured in a 2.5-mm thick TEFLON mold sandwiched between a sheet of polyester (PET) film and a glass slide for 30 seconds and cured with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure, n=5.

Depth of Cure Test Method

The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

Contrast Ratio (CR) Test Method & Color Test Method

Uncured samples were formed into 1 mm thick by 30 mm diameter disks using a stainless steel mold and a Carver press (10,000 to 15,000 psi). The disks were cured by exposing the disks to illumination from an LED array (455 nm wavelength, 850 mW/cm$^2$ intensity) for 20 seconds on one side of the disk. ASTM-D2805-95 (Hiding Power of Paints by Reflectometry) was modified to measure the contrast ratio (or opacity) of the disk. Y-tristimulus values for the disks of cured composite material were measured on a Color i7 spectrophotometer (X-Rite, Grand Rapids, MI, USA) with a 25 mm aperture using separate white and black backgrounds. All measurements were made in reflection mode with a D65 Illuminant with no filters. A 10 degree angle of view was used. Contrast ratio was calculated as the ratio of the Y-tristimulus of a cured sample through a black substrate to the Y-tristimulus through the identical sample on a white substrate (CR=RB/RW×100) in reflectance (i.e., reflectance is defined as equal to the Y-tristimulus value). Reported contrast ratio values are from single measurements unless otherwise noted, with lower values indicative of greater translucency (i.e., transmission of light). Color data (L*a*b*) was collected on the same spectrophotometer (25 mm aperture against a white background in reflectance mode with a D65 illuminant with no filters, 10 degree angle of view, excluding specular reflection), 2-10 minutes after cure.

Viscosity ($\eta$)

The viscosity can be measured with a Haake RotoVisco RV1 device (rotor C60/1 for viscosities up to 8000 mPas or rotor C20/1 for viscosities above 8000 mPas together with stator P61), as described in U.S. Pat. No. 9,295,617. The viscosity results in Table 4 were measured at 25° C.

Test Results

TABLE 2

| Test | Comparative Example C1 | Example 1 | Example 2 | Example 3 |
| --- | --- | --- | --- | --- |
| Stress (Cusp Deflection) (μm); n = 3 | 6.72 | 4.23 | 4.22 | 3.48 |
| DTS (MPa); n = 8 | 72.7 | 63.9* | 68.9 | 58.4 |
| Barcol Hardness (top); n = 5 | 92.0 | 95.4 | 93.6 | 93.2 |
| Barcol Hardness (bottom); n = 5 | 95.6 | 95.8 | 92.8 | 94.0 |
| Depth of Cure (mm); n = 3 | 11.67 | 11.80 | 11.45 | 10.87** |

*n = 6;

**n = 4

TABLE 3

Color Results

| | Comparative Example C1 | Example 1 | Example 2 | Example 3 |
|---|---|---|---|---|
| Weight (grams) | 1.4056 | 1.4055 | 1.4046 | 1.4060 |
| Thickness (mm) | 1.001 | 1.009 | 1.004 | 1.007 |
| L* | 91.27 | 91.24 | 90.65 | 90.61 |
| a* | −1.78 | −1.35 | −1.32 | −1.28 |
| b* | 6.57 | 4.88 | 5.18 | 5.17 |
| Opacity (Contrast Ratio) | 32.82 | 40.61 | 41.96 | 43.57 |

TABLE 4

Viscosity Results

| Sample | Viscosity Average, Pa·S, at 25° C. | MW |
|---|---|---|
| BISGMA | 1017.7 | 512.60 |
| Preparatory Example A (BHEPF-IEEMA Urethane) | 3223.4 | 836.92 |
| Preparatory Example C (Miramer HR6200 Butylamine IEMA Urea) | 26.4 | 1796.13 |
| Preparatory Example D (Miramer HR6200 Butylamine IEEMA Urea) | 15.7 | 1884.24 |
| Preparatory Example F (Miramer HR6060 Butylamine IEMA Urea) | 2256.7 | 1179.40 |
| Preparatory Example G (Miramer HR6060 Butylamine IEEMA Urea) | 209.3 | 1267.50 |

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A curable dental composition comprising:
a compound having structural formula (A):

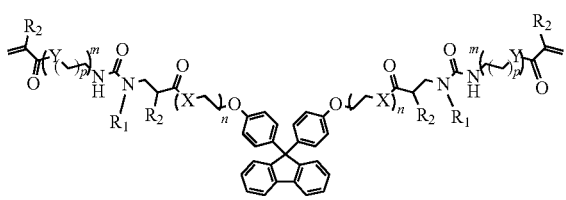

(A)

where

X is an amine-, oxygen-, or sulfur-containing linkage;
Y is an amine-, oxygen-, or sulfur-containing linkage;
n is 1-15;
m is 1-5;
p is 1-5, with the proviso that when p is greater than 1, m is 1;
each $R_1$ is, independently, an alkyl or aryl group having 2 to 20 carbon atoms that is linear, branched, cyclic, or some combination thereof, and optionally includes one or more heteroatoms or unsaturated bonds; and
each $R_2$ is, independently, a hydrogen atom or $CH_3$; and
filler, wherein filler is present in the curable dental composition in an amount of at least 25 wt.-%, based on the total weight of the curable dental composition.

2. The curable dental composition of claim 1, wherein at least one $R_1$ is selected from

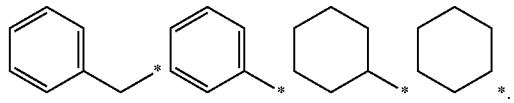

3. The curable dental composition of claim 1, wherein n is 1-10.

4. The curable dental composition of claim 1, wherein m is 1-3.

5. The curable dental composition of claim 1, wherein $R_1$ has 4 to 7 carbon atoms.

6. The curable dental composition of claim 1, wherein the compound having structural formula (A) is present in the curable composition in an amount of at least 5 wt.-%, based on the total weight of the curable dental composition.

7. The curable dental composition of claim 1, wherein the refractive index of the compound having structural formula (A) is between 1.53 and 1.60 ($n_D^{20}$).

8. The curable dental composition of claim 1, wherein the viscosity of compound (A) is no more than 3500 Pa*s at 25 degrees Celsius.

9. The curable dental composition of claim 1, wherein the refractive index of a reaction product of the curable components of the curable composition inclusive of filler having a particle size of 100 nm or less differs from the refreactive index of the filler by less than 0.05.

10. A method comprising producing a dental cement, a crown and bridge material, a dental filling material, a casting material, a cavity liner, a coating composition, a mill blank, an orthodontic devices, a sealant or combinations thereof using the curable composition of claim 1.

11. An article comprising a cured composition, wherein the cured composition is the reaction product of the curable dental composition according to claim 1.

* * * * *